United States Patent
Frings et al.

(10) Patent No.: US 6,398,917 B1
(45) Date of Patent: Jun. 4, 2002

(54) APPARATUS FOR THE PURIFICATION OF COMMERCIALLY AVAILABLE DIPHENYL-P-PHENYLENEDIAMINE (DPPD)

(75) Inventors: Albert-Johannes Frings; Michael Horn; Peter Jenker; Jaroslaw Monkiewicz, all of Rheinfelden; Hans-Guenther Srebny, Duelmen; Burkhard Standke, Loerrach; Bertram Trautvetter, Rheinfelden, all of (DE)

(73) Assignee: Degussa-Huels Aktiengesellschaft, Frankfurt (DE)

( * ) Notice: Subject to any disclaimer, the term of this patent is extended or adjusted under 35 U.S.C. 154(b) by 0 days.

(21) Appl. No.: 09/480,481

(22) Filed: Jan. 11, 2000

Related U.S. Application Data

(62) Division of application No. 09/301,601, filed on Apr. 29, 1999, now Pat. No. 6,026,880, which is a division of application No. 09/004,851, filed on Jan. 9, 1998, now Pat. No. 5,945,554, which is a division of application No. 08/777,702, filed on Dec. 20, 1996, now Pat. No. 5,763,666.

(30) Foreign Application Priority Data

Dec. 28, 1995 (DE) .......................... 195 49 032

(51) Int. Cl.$^7$ .......................... B01D 3/00; B01D 11/00; B01D 15/00; C07C 209/84
(52) U.S. Cl. ............. 202/168; 202/169; 202/203; 203/41; 203/43; 203/DIG. 16; 210/295; 210/664; 564/437
(58) Field of Search ............... 203/41–47, DIG. 16; 202/168, 169, 183–184, 200, 203, 158, 262; 210/348, 607, 295, 664; 564/434, 437

(56) References Cited

U.S. PATENT DOCUMENTS

| | | | |
|---|---|---|---|
| 2,744,938 A | | 5/1956 | Urban, Jr. |
| 2,833,824 A | * | 5/1958 | Pecherer ..................... 564/434 |
| 4,946,977 A | | 8/1990 | Bernhardt et al. |
| 5,279,747 A | * | 1/1994 | Chu ........................... 210/751 |
| 5,565,066 A | * | 10/1996 | Marker et al. .............. 202/158 |
| 5,763,666 A | | 6/1998 | Frings et al. |
| 5,945,554 A | | 8/1999 | Frings et al. |
| 6,026,880 A | | 2/2000 | Frings et al. |
| 6,063,242 A | * | 5/2000 | Hauser ....................... 202/205 |

FOREIGN PATENT DOCUMENTS

| | | |
|---|---|---|
| DE | 38 32 621 | 9/1989 |
| JP | 3166241 A | 7/1991 |

OTHER PUBLICATIONS

Mustafa Al–Jarrah et al J. Pet Res. (1988) 7(2) 73–86.
Chakravarty, S et al Rubber News (1974) 14(1) 22–7.
Chemical Abstracts, vol. 89, 1978, AN–23925.
Beilstein E III 13, 4$^{th}$ Auflage, 1973.
The Merck Index, Ninth Edition, 1976, p. 445.

\* cited by examiner

*Primary Examiner*—Virginia Manoharan
(74) *Attorney, Agent, or Firm*—Oblon, Spivak, McClelland, Maier & Neustadt, P.C.

(57) ABSTRACT

An apparatus for the purification of crude N,N'-diphenyl-p-phenylenediamine (DPPD) in which there is an extraction unit containing a liquid permeable container and an adsorption layer downstream of the container, a solvent evaporator downstream of the adsorption layer, a filter unit, a line for returning the filtrate to the solvent evaporator, and a condenser for returning solvent to the extraction unit.

5 Claims, 2 Drawing Sheets

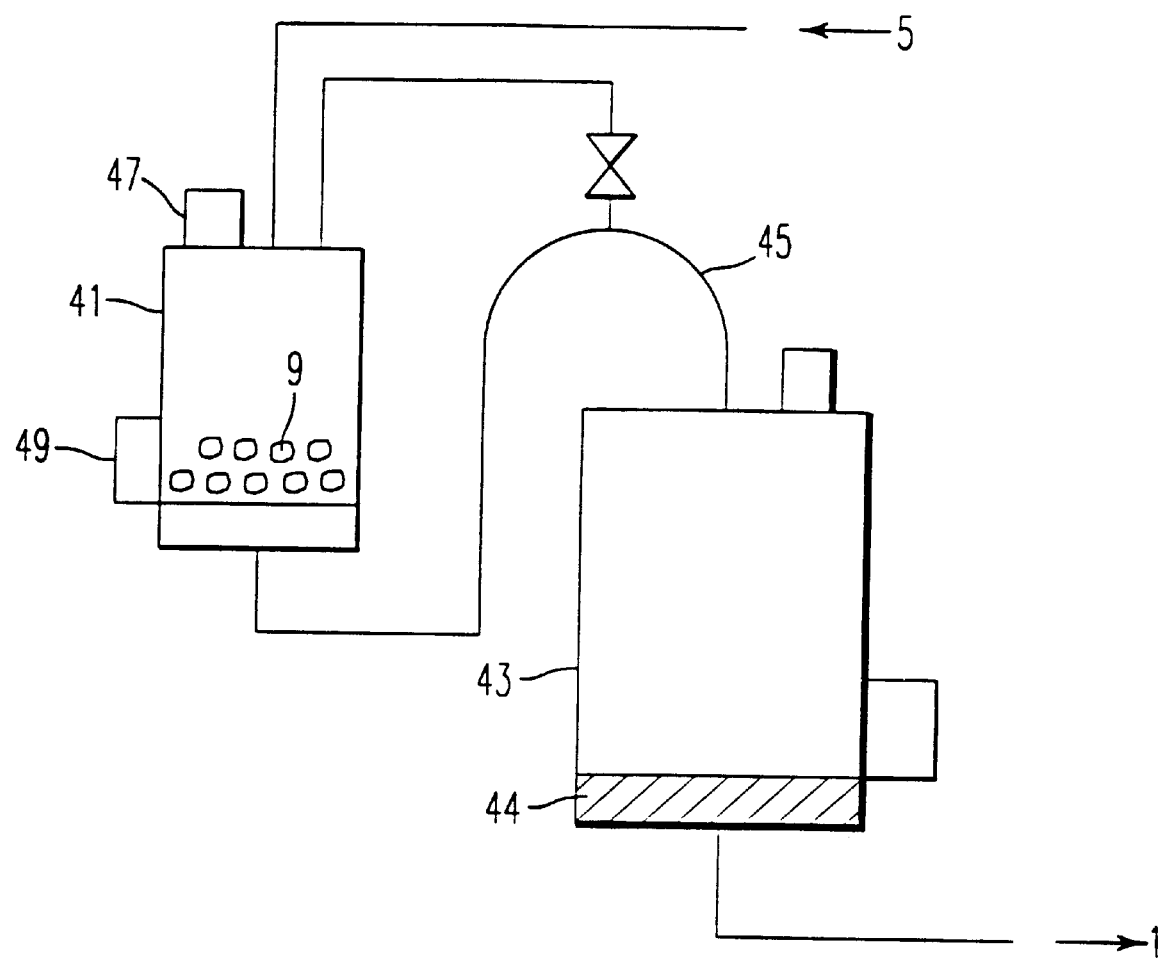

APPARATUS FOR THE PURIFICATION OF COMMERCIALLY AVAILABLE DIPHENYL-P-PHENYLENEDIAMINE (DPPD)

BACKGROUND OF THE INVENTION

This application is a Division of application Ser. No. 09/301,601 Filed on Apr. 29, 1999, now U.S. Pat. No. 6,026,880, which is a Divisional of application Ser. No. 09/004,851, filed Jan. 9, 1998, now U.S. Pat. No. 5,945,554, which is a Divisional of application Ser. No. 08/777,702, filed Dec. 20, 1996, now U.S. Pat. No. 5,763,666.

1. Field of the Invention

The present invention relates to a process and to an apparatus for the purification of crude diphenyl-p-phenylenediamine (DPPD) and to the use of purified DPPD.

DESCRIPTION OF THE BACKGROUND

DPPD is used on a large industrial scale as a stabilizer, inter alia, in the reaction of potassium methacrylate with 3-chloropropyltrimethoxysilane. In this application, the use of commercially available DPPD can impair product quality, in particular the color number of the product. Unfortunately, in the past, industrial quantities of DPPD have only been available on the market in a technical quality.

Crude DPPD, that is, commercially available DPPD or technically pure DPPD, has, as a rule, a purity in the range around 85% by weight, the remainder of about 15% by weight essentially consisting of unconverted or incompletely converted starting materials such as, for example, diphenylamine, and of inorganic components such as iron and chlorine, for example in the form of iron chloride. The commercial material is gray and is often in the form of a powder or in the form of flakes. In contrast thereto, pure DPPD is white and crystalline.

Several methods for the purification of DPPD are described in the literature. It is possible to crystallize DPPD from chlorinated hydrocarbons or carbon tetrachloride (Beilstein E III 13, 4$^{th}$ Auflage 1973, pages 115–118, The Merck Index, 9$^{th}$ Edition 1976, page 445). The disadvantage of these processes is, however, the use of chlorinated solvents which are toxic and pollute the environment.

Another purification method is solids distillation. This method can be applied successfully in the laboratory. For the purification of crude DPPD on an industrial scale, however, solids distillation is not a suitable process, since it is too expensive in engineering terms. A need therefore continues to exist for a method of inexpensively and effectively purifying DPPD.

SUMMARY OF THE INVENTION

Accordingly, one object of the present invention is to provide a process which allows crude DPPD to be purified in a simple and economical manner, thereby making a purified DPPD product available for application on an industrial scale.

Briefly, this object and other objects of the present invention as hereinafter will become more readily apparent can be attained in a process for purifying crude N,N'-diphenyl-p-phenylenediamine (DPPD), comprising extracting crude DPPD with a hydrocarbon or hydrocarbon mixture, passing the extract over an adsorption layer and recovering purified DPPD from this solution. Preferably, the purification is carried out under a blanketing gas.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 2 is a flow diagram of a preferred embodiment of the apparatus arrangement of the extraction unit of the flow process shown in FIG. 1.

DETAILED DESCRIPTION OF THE PREFERRED EMBODIMENTS

Figure 1:
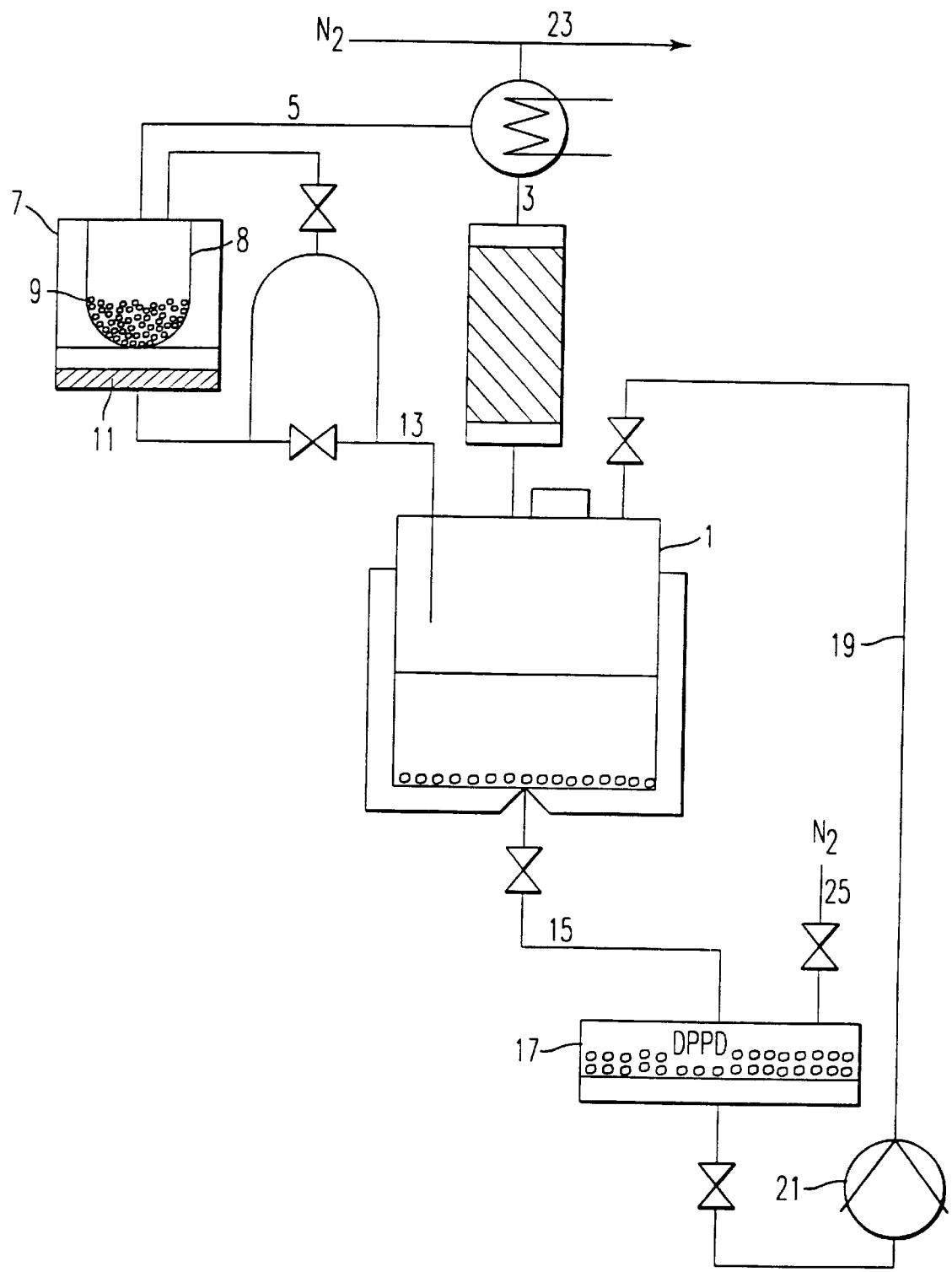
FIG. 1 is a flow diagram showing apparatus components of a preferred embodiment of the invention for purifying DPPD.

Surprisingly, it has now been found that, by extracting crude DPPD with a hydrocarbon or a mixture of hydrocarbons and passing the extract over an adsorption layer, pure DPPD, preferably white and in crystalline form, is obtained in a simple and economical manner from the solution which has been prepared. In the present process, industrial DPPD can also be used as the crude DPPD.

FIG. 1 shows the flow diagram of a preferred embodiment of the equipment in which the process of the invention can be carried out.

The apparatus for the purification of N,N'-diphenyl-p-phenylenediamine (DPPD) comprises a solvent evaporator (1) to which is attached a downstream condenser (3) which is connected via a solvent line (5) to an extraction unit (7) which in turn is equipped with an interior and liquid-permeable container (8) in which DPPD is extracted from crude DPPD (9) and with a downstream adsorption layer (11). Layer (11) is connected via an extract line (13) to the solvent evaporator (1) which in turn is coupled at the bottom via a lock (15) to a filter unit (17). A filtrate line (19) leads via a pump (21) to the solvent evaporator (1). Suitably, one or more blanketing gas line(s) (23) and/or (25) are also provided in the apparatus.

The apparatus embodiment, shown in FIG. 2, is a preferred embodiment of the extraction unit and employs extraction vessel (41) in which DPPD is extracted from crude DPPD (9) and a vessel (43) which is connected thereto via a line system (45) and which contains an adsorbent layer 44. Suitable, the extraction unit is equipped with a crude produce feeder (47) and/or a residue outlet (49). Furthermore, however, the solvent evaporator (1), the extraction unit (7) and the filtration unit (17) can also be equipped with a material feeder lock or a material removal lock.

In order to achieve more thorough mixing in the relevant solid/liquid phases or also better heat transfer in the liquid phases, the apparatus of the invention can also be equipped, with respect to units (9), (41) and (1), with a stirrer or mixer unit.

For the recovery of purified DPPD, the present apparatus can also be equipped, in place of filtration unit (17), with other separation devices, known per se for the separation of solid/liquid systems, such as a centrifuge or a decanter.

In general, the process of the invention is carried out as follows:

Hydrocarbons or hydrocarbon mixtures can initially be introduced into the solvent evaporator (1). The quantity of extractant introduced here depends as a rule on the size of the apparatus or unit available.

In general, all cyclic, aliphatic or aromatic, but also acyclic branched or unbranched hydrocarbons having 3 to 10 carbon atoms are suitable as extracting solvents. For carrying out the extraction, preferably pentane, cyclopentane, hexane, cyclohexane, benzene, toluene, heptane, cycloheptane and many others are used. In the process of the invention, the extraction is carried out with particular preference for hexane, which includes all of its isomers and isomer mixtures. However, unsaturated cyclic or acyclic hydrocarbons such as cyclopentene, pentene, cyclohexene, cyclohexadiene, hexene and many others, can also be used as extractants in the process. Likewise, mixtures of aliphatically saturated, aliphatically unsaturated, cyclic, acyclic and aromatic hydrocarbons can also be used.

As a rule, the solvent evaporator (1) is operated under normal pressure at a temperature in the range from 40 to 110° C. The solvent fraction thus transferred into the gas phase is suitable passed through a condenser (3) and the condensate which forms is fed via a solvent line to the extraction vessel (7).

The extraction containers (8) and (41), which are permeable to liquids, of the extraction unit can consist of a textile fabric which can be made of a polyester, polyamide or another polymer, and/or can consist of a metal fabric. The mesh width of such fabrics is usually in the range from 0.01 to 0.2 mm. The extraction vessel, which is permeable to liquids, and/or the bottom for taking up an adsorbent can, however, also consist of ceramic materials, for example of G1–G4 fritted glass.

The part of each absorption layer (11) and (44), which is suitably equipped with a liquid-permeable bottom, can be covered by a layer of adsorbent. The adsorbent used in the process of the invention is preferably silica gel, for example a silica gel made by MERCK. For such adsorption layers, layer thicknesses in the range of from 2 cm to 30 cm are preferred, but the layers can also be thicker. Thus, for example a silica gel having a mean grain size of from 0.063 to 3.00 mm can be used here, and the silica gel preferably used has a mean grain size from 0.063 to 0.5 mm. A particularly preferred silica gel is a silica gel having a mean grain size from 0.20 mm to 0.5 mm. In particular a silica gel having a BET surface area of from 450 to 550 $m^2/g$. A liquid-permeable extraction vessel (8) filled with commercially available DPPD can be located above the adsorption layer (11). The extraction unit (7) prepared in this way is in general sealed gas-tight to form a gas-tight enclosure and charged via the condensate line (5) with solvent.

The extraction vessel (8) and the vessel for the adsorbent layer (11) can of course also be arranged separate from one another, in which case the crude extract can be fed from the extraction vessel (41) via a line (45) to the adsorbent vessel (43) which contains adsorbent layer 44. A preferred embodiment for this purpose is shown in FIG. 2.

Suitably, the crude DPPD first introduced into the extraction vessel (8) or also into unit (41) is covered with extractant. However, the extraction vessels (8) and (41) as a rule are filled up to a level which corresponds to the highest point in the extract discharge (13) or (45). When this level is reached, the extract flows off because of the siphoning effect into the solvent evaporator (1) or via the vessel (43) into the solvent evaporator (1).

In the process of the invention, the extraction is generally carried out at a temperature in the range of from 40 to 100° C. The adsorption is as a rule also carried out at a temperature in the of range from 40 to 100° C.

In a suitable manner, the adsorption layers (11) and (44) then take up particles present in the extract and impurities which cause turbidity, so that the solution flowing off into the solvent evaporator (1) is clear. The process of the invention can be carried out under normal pressure, at reduced pressure or even at slightly elevated pressure.

It has been found that it can be expedient to insulate the extraction unit (7), as well as units (41) and (43), including the lines (45), as well as (13) and (15) against heat losses. It is also possible to provide trace-heating for the extraction unit (7), as well as units (41) and (43) including the lines (45), as well as units (13) and (15).

Crude DPPD (9) can be charged to the extraction vessels (8) and (41) discontinuously or continuously. Especially for carrying out the process of the invention continuously, the extraction vessels (8) and (41) can be equipped with a product-charging device for crude DPPD, for example, (47), and a discharge device for the extraction residue, for example, (49). The adsorbent vessels, for example, (43) can also be equipped with suitable locks for the removal of spend silica gel and for the charging of fresh silica gel. Such an arrangement is advantageous for increasing the plant capacity for the production of purified DPPD.

The equipment of the invention is advantageously blanketed with inert gas, for example nitrogen (23) and (25), in order to prevent the formation of ignitable mixtures.

After several extraction cycles, the purification of DPPD can be observed by how it crystallizes as a white microcrystalline powder from the supersaturated solution in the solvent evaporator (1).

The process of the invention for the purification of crude DPPD can be carried out discontinuously or continuously. In discontinuous operation of the unit, the extraction vessel (8) or (41) is suitably emptied and refilled with crude DPPD several times before the extraction is stopped and the purified product is isolated from the extractant. In this case, 2 or 3 emptying and filling steps are preferred before the pure DPPD is isolated. The adsorption layer (11) or (44) can be partially or completely replaced. It is, however, also possible to run several extractions through the same adsorption layer, without impurities passing into the solvent evaporator (1). The extraction period is as a rule 20 to 60 hours, so that in general the mean residence time of the product in the purification process is also 20 to 60 hours. Experience shows that an extraction period of about 35 hours is to be preferred from the viewpoint of space/time yields. In the process of the invention, yields of 60 to 85%, relative to the crude DPPD employed, are generally achieved, which is to say that the process of the invention can also be operated without a loss of valuable product.

After termination of the extraction, the suspension consisting of extractant and purified crystalline DPPD is, for example, drained onto a filter (17) and separated. The filtrate is clear and can in general be used for further extractions, even without further purification (compare 19 and 21). However, the filtrate can also first be distilled before re-use.

The purified DPPD present can, for example, be dried in vacuo or isolated, under a stream of nitrogen, as a white to light-beige microcrystalline powder. The product purified by the process of the invention has in general a purity of >90%, preferably >95% and very particularly preferably 97 to 99% (determination by NMR spectroscopy). The DPPD purified by the invention preferably has a melting range in the temperature range of from 142° C. to 154° C., and purified DPPD having a melting range in the temperature range of from 144° C. to 148° C. is particularly preferred. In contrast thereto, the commercially available crude DPPD, having a purity of about 85%, has a melting range of from 124 to 126° C.

When DPPD purified by the process of the invention is employed, for example, for the stabilization of MEMO (3-methacryloxypropyltrimethoxysilane) (compare German Patent Specification 3,832,621), the product thus obtained is distinguished by a particularly outstanding color number.

Another aspect of the invention is the use of DPPD, purified by the process of the invention, for the stabilization of organosilanes, containing methacryloxy or acryloxy groups, of the formula I

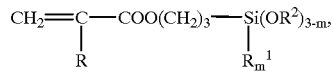

wherein R is a hydrogen atom or a methyl group, $R^1$ and $R^2$ are identical or different alkyl groups having 1 to 4 C atoms or phenyl groups and m is equal to 0, 1 or 2.

The purified DPPD of the invention can also be used in tire manufacture.

A further advantage of the process of the invention is that, because of the use of largely non-polluting hydrocarbons, methods using chlorinated hydrocarbons as extractants do not have to be employed.

Having generally described this invention, a further understanding can be obtained by reference to certain specific examples which are provided herein for purposes of illustration only and are not intended to be limiting unless otherwise specified.

EXAMPLE 1

An extraction vessel, fitted with a liquid-permeable bottom, is filled with 5.5 kg of silica gel 60 (grain size 0.2 to 0.5 mm) made by MERCK, which is mixed with 4 kg of ceramic saddle-type packing having a diameter of 15 mm. Above this adsorption layer, a liquid-permeable extraction vessel containing 10 kg of crude DPPD made by GOBEL and PFRENGLE is suspended from the lid of the extraction vessel.

300 l of hexane (an isomer mixture having a boiling point of 68° C.), manufactured by OLFABRIK Lahr, is first introduced into the solvent evaporator. The unit is permanently blanketed with dry nitrogen, so that atmospheric oxygen and atmospheric humidity can be excluded.

The extractant is heated to the boil. A temperature of 68° C. is measured at the base of the extraction unit. The condensate flows via the condensate line into the extraction vessel and from there, depending on the filling level in the extraction vessel, with dissolved DPPD back into the solvent evaporator. The extraction cycles are repeated over a period of 60 hours. The extraction unit is then opened to remove the extraction vessel. The residue is removed from the extraction vessel. Weighing after drying gives a quantity of 1.5 kg of residue. The silica gel is replaced by 6 kg of fresh silica gel containing 4 kg of saddle-type packing. The extraction vessel filled with 10 kg of crude DPPD is reinserted into the extraction vessel. After an extraction period of 36 hours, 1.5 kg of residue are obtained.

The content from the solvent evaporator is drained onto a filter. The filter cake is washed twice with about 18 kg of hexane and dried in vacuo with a little nitrogen being introduced simultaneously. This procedure provides 16 kg of pure DPPD as a light-beige microcrystalline powder. This corresponds to a yield of 80%, relative to the total quantity of crude DPPD employed.

EXAMPLE 2

Quantities employed for one extraction:
i) 4 kg of silica gel 60 (0.2 to 0.5 mm)=55 mm layer height,
ii) 1.5 kg of used silica gel (yellow)=25 mm layer height,
iii) 4 kg of saddle-type packing: Total height of the adsorption layer=80 mm,
iv) 400 l of hexane (isomer mixture),
v) 9 kg of crude DPPD (flakes).

After an extraction period of 40.5 hours, the amount of residue was 2.5 kg and the amount of extracted DPPD was 6.5 kg.

EXAMPLE 3

Quantities employed for the first extraction:
i) 4 kg of silica gel,
ii) 1.5 kg of used silica gel,
iii) 9 kg of crude DPPD (powder),
iv) 400 l of hexane.

Quantities employed for the second extraction:
i) 3 kg of unused silica gel 60,
ii) 3 kg of used silica gel 60,
iii) 4 kg of saddle-type packing
iv) 10 kg of crude DPPD (flakes)

From 19 kg of crude DPPD, 12.5 kg=67% of pure DPPD were isolated in the form of a white powder.

Having now fully described the invention, it will be apparent to one of ordinary skill in the art that many changes and modifications can be made thereto without departing from the spirit or scope of the invention as set forth herein.

What is claimed is:

1. An apparatus for the purification of N,N'-diphenyl-p-phenylenediamine (DPPD), which comprises:
   an extraction unit, said extraction unit comprising
   a liquid-permeable container in which DPPD is extracted from crude DPPD placed therein and a downstream adsorption layer comprising an adsorbent,
   a solvent evaporator downstream of the adsorption layer in the extraction unit,
   a filter unit downstream of the solvent evaporator,
   a lock in a line connecting the solvent evaporator to the filter unit,
   a filtrate line from the filter unit, in which there is a pump leading to the solvent evaporator,
   a condenser downstream of the solvent evaporator for recovering and condensing the gas phase from the solvent evaporator, and
   a solvent line for returning the condensed gas phase from the condenser to the extraction unit upstream of the liquid-permeable container.

2. The apparatus as claimed in claim 1, which has at least one blanketing gas line which provides an inert atmosphere.

3. The apparatus as claimed in claim 1, wherein the extraction unit comprises the liquid-permeable container in which DPPD is extracted from crude DPPD, which comprises a liquid-permeable extraction vessel, and a vessel downstream of the liquid-permeable extraction vessel which is connected thereto via a line and which contains the adsorbent of the adsorption layer.

4. The apparatus as claimed in claim 1 wherein said extraction unit is a gas-tight enclosure comprising the liquid permeable container in which DPPD is extracted from crude DPPD in the interior of the enclosure and the downstream adsorption layer in the interior of the enclosure.

5. An apparatus for the purification of N,N'-diphenyl-p-phenylenediamine (DPPD), which comprises:
   an extraction unit, said extraction unit comprising a liquid-permeable container in which DPPD is extracted from crude DPPD placed therein and a downstream adsorption layer comprising an adsorbent, a solvent evaporator downstream of the adsorption layer in the extraction unit, a filter unit downstream of the solvent evaporator, a lock in a line connecting the solvent evaporator to the filter unit, a filtrate line from the filter unit leading to the solvent evaporator, a condenser downstream of the solvent evaporator for recovering and condensing the gas phase from the solvent evaporator, and a solvent line for returning the condensed gas phase from the condenser to the extraction unit upstream of the liquid-permeable container, the extraction unit comprising a vessel downstream of a liquid-permeable extraction vessel and connected thereto via a line and which contains the adsorbent of the adsorption layer, the extraction vessel further comprising a crude product feeder and/or a residue outlet.

* * * * *

UNITED STATES PATENT AND TRADEMARK OFFICE
CERTIFICATE OF CORRECTION

PATENT NO. : 6,398,917 B1
DATED : June 4, 2002
INVENTOR(S) : Frings et al.

It is certified that error appears in the above-identified patent and that said Letters Patent is hereby corrected as shown below:

<u>Title page,</u>
Item [45] and the Notice information should read as follows:
-- [45]  Date of Patent:     *Jun. 4, 2002
  [*]   Notice: This patent issued on a continued prosecution
        application filed under 37 CFR 1.53(d), and is
        subject to the twenty year patent term provisions
        of 35 U.S.C 154(a)(2).

Subject to any disclaimer, the term of this
        patent is extended or adjusted under 35
        U.S.C. 154(b) by 0 days. --

Signed and Sealed this

Fifteenth Day of October, 2002

*Attest:*

*Attesting Officer*

JAMES E. ROGAN
*Director of the United States Patent and Trademark Office*